United States Patent [19]
Rooney

[11] Patent Number: 5,910,449
[45] Date of Patent: *Jun. 8, 1999

[54] ASSESSMENT OF CHARACTERISTICS OF FLUIDS

[75] Inventor: Matthew Jonathan Rooney, West Bridgford, United Kingdom

[73] Assignee: Naked Eye Limited, United Kingdom

[*] Notice: This patent is subject to a terminal disclaimer.

[21] Appl. No.: 08/712,044

[22] Filed: May 24, 1996

Related U.S. Application Data

[63] Continuation-in-part of application No. 08/256,654, filed as application No. PCT/GB93/00151, Aug. 29, 1994, Pat. No. 5,538,900.

[30] Foreign Application Priority Data

Jan. 22, 1992 [GB] United Kingdom ................ 92 01 348

[51] Int. Cl.$^6$ .................................................. G01N 21/03
[52] U.S. Cl. .............................. 436/165; 436/63; 436/66; 422/55; 422/58; 422/82.05; 422/102
[58] Field of Search ............................ 436/63, 66, 165; 422/55, 58, 82.05, 99, 102

[56] References Cited

U.S. PATENT DOCUMENTS 5,125,748   6/1992   Bjornson et al. ...................... 356/414
5,538,900   7/1996   Rooney ................................... 436/165

FOREIGN PATENT DOCUMENTS 5862542    4/1983   Japan ..................................... 422/73
59168364   9/1984   Japan ..................................... 422/73

OTHER PUBLICATIONS

Fiddik et al., "A variable pathlength ... " Journal of Physics E. Scientific Instruments vol. 21, No. 11, Nov. 1988.

Hirschfeld "Lens and Wedge ... " Applied Spectroscopy vol. 39, No. 3 Jun. 1985.

*Primary Examiner*—Harold Y. Pyon
*Attorney, Agent, or Firm*—Galgano & Burke

[57] ABSTRACT

The invention relates to an apparatus for measuring the ability of a fluid to transmit radiation therethrough, the apparatus comprises a chamber for receiving the fluid and associated means for examining the transmission of radiation through the fluid at different parts of the chamber given that the means is adapted to differentially facilitate an examination of said transmission at different parts of the chamber.

21 Claims, 4 Drawing Sheets

ASSESSMENT OF CHARACTERISTICS OF FLUIDS

This is a Continuation-in-Part of application Ser. No. 08/256,654, filed Aug. 29, 1994, issued Jul. 23, 1996 as U.S. Pat. No. 5,538,900, which is a 371 of PCT/GB93/00151 Aug. 29, 1994.

BACKGROUND OF THE INVENTION

This invention relates to a method of, and apparatus for, assessing characteristics of fluids. More particularly, it relates to the quantitative assessment of a change in a fluid, e.g. dilution or contamination thereof, or chemical change therein, which change alters the characteristics of the fluid with respect to transmission of radiation therethrough.

The invention is particularly applicable to the assessment of the concentration of a substance present in a fluid, the fluid being relatively transparent to radiation and the substance in the fluid causing an increasing resistance to the passage of radiation through the fluid as its concentration increases. The invention has been devised in relation to the situation wherein the fluid is a liquid and the substance therein is another liquid, such two liquids respectively being substantially transparent to visible light and resistant to the passage of visible light therethrough, such that increasing concentration of the latter liquid in the former liquid causes a progressive decrease in the transparency of the mixed liquids to light. However, it will be appreciated that the principle of the invention is also applicable when the substance whose concentration is required to be assessed is a solid which may form a solution or suspension in the liquid to cause a progressive decrease in the transparency of the liquid with increasing concentration of the solid. The principle of the invention is also applicable to mixtures of gases or vapours wherein a change in the concentration of one such gas or vapour in another causes a change in the transparency of the mixture to light or other radiation, or to the presence of particles in gases, e.g. smoke.

Some examples of applications of the invention are set forth hereafter, but the invention has been devised in relation to a requirement which exists in the medical field, namely that of assessing the quantity of blood contained in a liquid which otherwise comprises wholly or mainly water. A typical situation in which the requirement arises is that where surgery is performed on the prostate glad of a patient. It is important to know how much of the patient's blood is lost in order to asses the need for replacement thereof by transfusion, but direct measurement of such blood loss is extremely difficult because, although fluid can be collected by a catheter inserted into the bladder of the patient, such fluid comprises blood mixed with some urine from the patient's bladder and irrigation fluid, which is mainly water, introduced into the patient's bladder. The drained fluid, collected in a catheter bag, can be subjected to laboratory analysis to determine the concentration of blood therein, and thus the requirement for replacement of blood, but such analysis is time consuming and expensive. Furthermore, highly accurate analysis is not necessary for the immediate purpose of assessing the requirement for replacement blood. There is thus a requirement for a rapid and reasonably accurate assessment of the concentration of blood in the drained fluid to be made; then, since the total volume of fluid in a catheter bag is readily measured, it is possible to make a virtually immediate assessment of any requirement for blood replacement

SUMMARY OF THE INVENTION

It is one object of the present invention to meet the above described requirement for assessment of concentration of blood in fluid drained from a patient. However, it will be appreciated that the principle of the invention, in meeting this requirement, is applicable far more widely, and examples of such application are referred to hereafter.

According to one aspect of the present invention, I provide apparatus for assessing a characteristic of a fluid in respect of its effect on the transmission of radiation through the fluid, comprising a chamber for receiving the fluid, said chamber including wall portions, arrange for passage of radiation therethrough and through fluid therebetween and means for examining the effect of transmission of the radiation through the fluid at different parts of the chamber, said means being adapted along at least one preselected axis so as to progressively facilitate an examination of the passage of radiation through the fluid whereby said characteristic can be assessed.

In a preferred embodiment of the invention said means comprises a pattern or marker which is spaced differently from said chamber along a preselected axis of said pattern or marker so that radiation travels different distances after passing through said chamber in order to interact with said pattern or marker.

It will be appreciated that at a part of the apparatus where the pattern or marker is spaced at a relatively small distance from the chamber, compared with a part where there is more spacing, the effect will be to facilitate an examination of passage of radiation through the fluid ie a reading will most easily be taken in the region where there is less spacing. In particular, amongst other things, attenuation of the radiation will be least in those parts of the apparatus where the radiation has to travel least distance in order to interact with the pattern or marker. The position in the apparatus at which radiation no longer, discernably, effectively interacts with the pattern or marker provides an indication of, amongst other things, the radiation-absorbing quality of the fluid.

In an alternative embodiment of the invention said means comprises a pattern or marker of a variable nature along a preselected axis and ideally a progressively variable nature such that the type or magnitude of interaction of radiation therewith varies along the length of the pattern or marker. For example, in the instance where the radiation is of visible nature the shading or colouring of the pattern may vary along its length in preselected manner, for example in uniform or non uniform manner.

It will be appreciated that at a part of the chamber where the brightness or colouring of the pattern or marker is strongest, as compared to another part with less brightness or colouring, the effect will be to facilitate an examination of passage or radiation through the fluid. In particular, absorbtion and/or reflection of radiation along the length of the pattern or marker can be selectively controlled so that, ideally, at a first end of the pattern or marker maximum detection of radiation interaction with the pattern or marker is achieved and at a second end minimal detection is achieved, with, ideally, a graduation therebetween. Thus, the position in the chamber at which detection reaches a predetermined value ie typically the pattern or marker is no longer visible, provides an indication of the radiation-absorbing quality of the fluid.

Moreover, the relative sensitivity of the apparatus can be controlled by selecting the maximum and minimum values of the pattern or marker; and/or the graduation therebetween. Thus, where a given concentration may be undetectable using one sort of pattern or marker because the concentration is effectively "off-the-scale" an alternative, more suitable, pattern or marker may be substituted so as to maximise the sensitivity of the apparatus with a view to making said assessment.

In yet an alternative embodiment of the invention said means comprises a pattern or marker of relatively uniform nature such as a bar of uniform colour and/or brightness, which is ideally positioned rearwardly of said chamber, and the said means further includes a window positioned forwardly of said chamber wherein said window is of a variable nature along a preselected axis and ideally a progressively variable nature for example in the instance where the radiation is visible radiation, the window is of variable transparency, ideally progressively from one end to the other, and more ideally of selected variation for example uniform or non uniform variation.

It will be appreciated that at a part of the chamber wherein the window is relatively less transparent and so approaching the opaque the rearward pattern will only just be visible, whereas at the opposite end where the window is of maximum transparency the pattern will be more easily viewed; therebetween a graduation in transparency is provided. The position in the chamber at which the visibility of the pattern reaches a predetermined value, ie typically is no longer visible, provides an indication of the radiation-absorbing quality of the fluid.

In other embodiments of the invention the transmissibility of the window will be variable ideally along its length so as to influence the amount of said radiation passing therethrough and so available for executing said assessment.

In yet a further alternative embodiment of the invention said means may include any combination of the above preferred embodiments of the invention, thus said means may include a pattern or marker spaced at a variable distance from said chamber and/or a front window of variable transmissibility and/or a pattern or marker of variable nature.

In yet a further embodiment of the invention said chamber may include wall portions that are spaced differently from one another at different parts of the chamber. This preferred embodiment of the invention may be provided in any one or more of the above preferred embodiments of the invention.

It will be appreciated that at a part of the chamber wherein the wall portions thereof are spaced at a greater distance from one another, compared with a part with a lesser spacing, the effect on the radiation being transmitted through the fluid between such wall portions will be greater. In particular, absorption of radiation by the fluid will be greater at a part of the chamber where the radiation has to travel a greater distance through the fluid. The position in the chamber at which absorption of radiation reaches a predetermined value provides an indication of the radiation-absorbing quality of the fluid.

Whilst it would be within the scope of the invention for the effect on transmission of ultra-violet or infra-red or other radiation (possibly sound, eg ultrasound, or possibly a magnetic field) through the fluid to be examined, the invention conveniently, but not exclusively, makes use of the effect on visible light of transmission thereof through the fluid. For example, in the situation above referred to wherein the concentration of blood in an aqueous liquid is required to be assessed, an increase in the concentration of blood causes a decrease in the transparency of the liquid to visible light.

When the effect on transmission of visible light through the fluid is being examined, this may conveniently be assessed visually by a user of the apparatus. The apparatus comprises a pattern or marker viewable through the wall portions of the chamber and the fluid contained therebetween, said pattern or marker having a visible marking, eg a design, pattern, colour, or other characteristic adapted to be distinguishable to the user viewing it through the chamber, the arrangement being such that at some point in the chamber such pattern or marker will no longer be clearly visible to the user, dependent on the brightness or colour of the pattern or maker and/or the transmissibility of a front window or panel and/or the distance between the pattern or marker and the chamber and/or the distance between the opposed chamber walls through which the user is looking. The position in the chamber at which the pattern or marker ceases to be clearly visible to the user therefore provides an indication of the degree to which the fluid has had its light-transmitting ability reduced by contamination or otherwise.

When the effect on transmission of ultraviolet light through the fluid is being examined, this may conveniently be assessed visually be a user of the apparatus. In this instance the apparatus comprises a pattern or marker viewable through the wall portions of the chamber and the fluid contained therebetween, said pattern or marker having ultraviolet properties, eg a UV design, UV pattern or other UV characteristic adapted to be distinguishable to the user viewing it through the chamber, the arrangement being such that at some point in the chamber such pattern or marker will no longer be clearly visible to the user, dependent on the brightness or UV density of the pattern or marker and/or the transmissibility of the front window or panel and/or the distance between the pattern or marker and the chamber and/or the distance between the opposed chamber walls through which the user is looking. Ideally, the apparatus is used in combination with an ultraviolet light source. The position in the chamber at which the pattern or marker ceases to be clearly visible to the user therefore provides an indication of the degree to which the fluid has had its light-transmitting ability reduced by contamination or otherwise.

The opposed wall portions of the chamber may have the spacing therebetween varying linearly, or in a curve or in some other manner, e.g. stepwise. For example, one wall portion may be planar while the other wall portion is in the shape of a curve, e.g. an exponential curve, approaching the first wall portion asymptotically from one end of the chamber to the other.

Preferably the apparatus is adapted to asses the concentration of a substance, which may be a solid or liquid, in a liquid. Thus the chamber may comprise, or form part of, a container adapted to have the liquid under investigation introduced therein and retained while a user carries out the assessment thereof.

A scale may be arranged along the chamber, adapted to provide a direct reading of concentration of the substance in the liquid in accordance with the position along the chamber at which the marking being viewed therethrough ceases to be clearly visible.

For the elimination or reduction of possible errors in looking through the chamber by the user, due to refraction at the wall portions thereof particularly if one such wall portion is curved, the chamber may be defined by a dividing wall portion provided in a container having substantially parallel opposite walls. Thus the container is divided into said chamber for receiving the fluid to be assessed, and a further chamber which preferably contains the uncontaminated fluid in which the concentration of the contaminating fluid is to be assessed.

Conveniently the concern including the dividing wall portion therein defining the two chambers, is a one-piece moulding of plastics material which is substantially transparent to visible light. The marking for observation by the user, and/or the scale may be provided on such container, or on another element adapted to be held or supported in relation to the container so as to be visible therethrough. It is envisaged that such apparatus according to the invention may be a "throw-way" item, intended to be used once only.

As above referred to, the invention has been devised for use in connection with the carrying out of a surgical operation. It is envisaged that apparatus according to the invention may be incorporated in or provided in operative association with a disposable catheter or catheter bag and according to another aspect of the invention I provide a catheter or catheter bag having apparatus according to the first aspect of the invention provided in operative association therewith, for assessing liquid flowing through or contained in the catheter or bag respectively.

Other features which may be provided in apparatus according to the invention are referred to in the following description with reference to the drawings.

According to another aspect of the invention, I provide a method of assessing a characteristic of a fluid in respect of its effect on the transmission of radiation through the fluid, comprising passing radiation through the fluid in an apparatus which is adapted along at least one pre-selected axis so as to progressively facilitate an examination of the passage of radiation through the fluid, and examining the effect of transmission of the radiation through the fluid at different parts of the chamber.

Preferably the radiation is visible light, or ultraviolet light and the method comprises visual observation through the chamber and fluid therein of a viewable element, and observing the position in the chamber at which such viewable element is no longer clearly discernable, such position providing an assessment of the relevant characteristics of the fluid.

Preferably the method is that of assessing the concentration of a substance in the fluid, the substance being one of which an increase in concentration thereof in the fluid causes a decrease in the transparency of the fluid to visible light.

The substance may be a first liquid, and the fluid a second liquid.

Further examples of applications of the invention include assessing contamination of cleaning fluids or of lubricants, e.g. engine oil. It is envisaged the invention will have application in the food industry, e.g. in the analysis of mixtures, e.g. milk/cream/water. The invention also has application to measurement of concentration of solution e.g. antifreeze or a dye, or in cases where a chemical reaction or test involving a chemical reaction produces a colour change in a liquid. Examples of such later include measurement of pH of a liquid involving a colour-changing indicator, or enzyme linked assays, e.g. immuno assays.

BRIEF DESCRIPTION OF THE DRAWINGS

The invention will now be described by way of example with reference to the accompanying drawings, of which.

DESCRIPTION OF THE PREFERRED EMBODIMENTS

Figures 1, 2, 3, 4, 5:
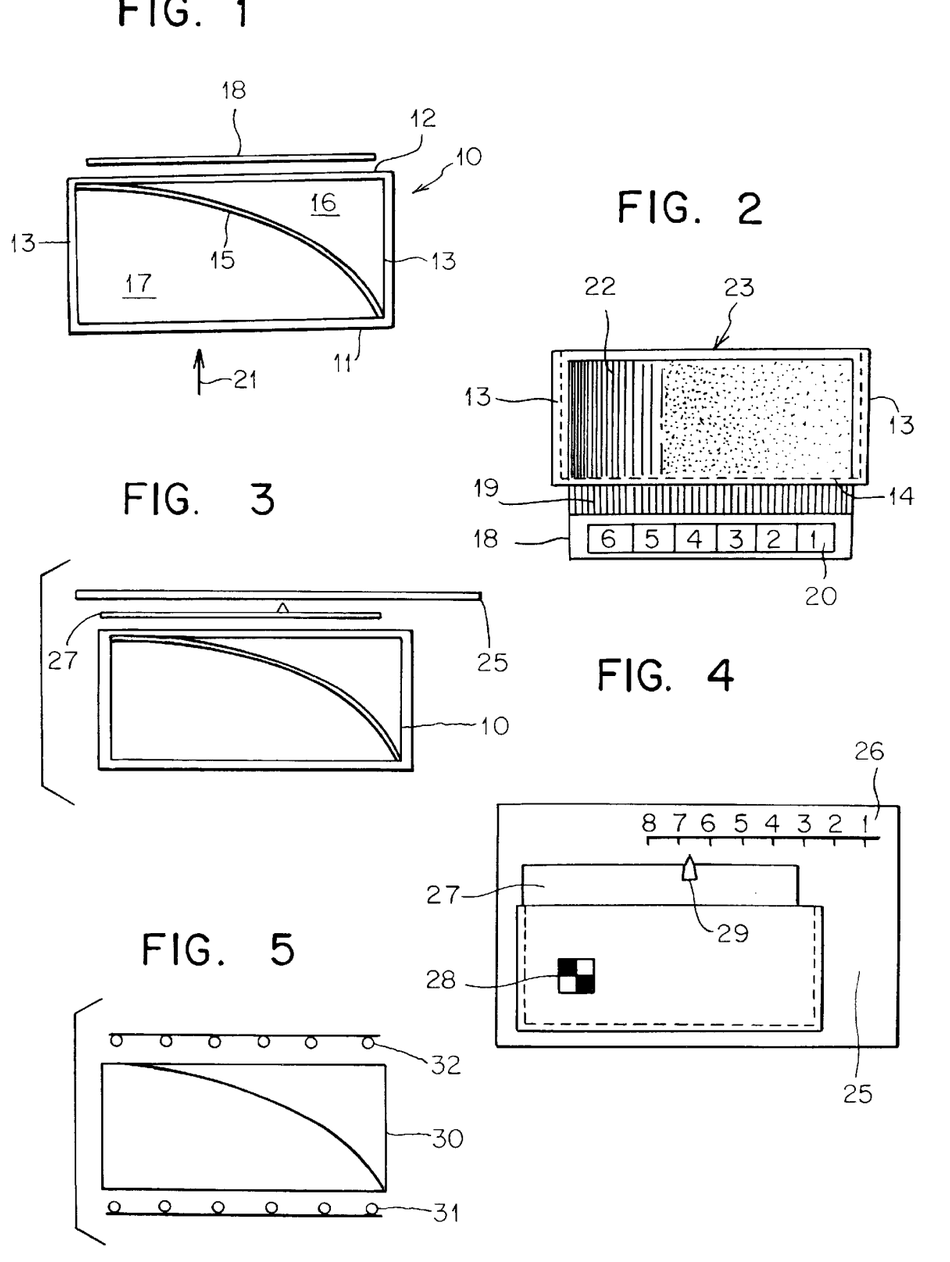
FIGS. 1 and 2 are respectively a plan view and a front elevation of a first embodiment of apparatus according to the invention.
FIGS. 3 and 4 are respectively a plan view and a front elevation of a further embodiment of apparatus according to the invention.
FIG. 5 is a diagrammatic plan view of a further embodiment of apparatus according to the invention.

Referring firstly to FIGS. 1 and 2 of the drawings, the embodiment of apparatus according to the invention shown therein is intended for assessing the concentration of a first liquid in a second liquid, the second liquid being substantially clear or not presenting any obstacle to transmission of light therethrough and the first liquid being, at least when present in the form of more than a layer of minimal thickness, substantially opaque to light of the intensity typically ambient in a working environment. By way of example, as in the example first referred to herein, the first liquid may be blood and the second liquid may be a clear aqueous solution, and it will be appreciated that as the concentration of blood in the clear liquid increases the resulting mixture of liquids becomes progressively less clear and more resistant to the passage of light therethrough. At a given concentration of the first liquid in the second liquid, transmission of light through the mixture of liquids decreases the greater is the distance that the light has to travel through the mixture of liquids.

The apparatus shown in FIGS. 1 and 2 comprises a container 10 which is generally of rectangular configuration both in elevation and plan, comprising a front wall 11; a rear wall 12; which walls are substantially parallel to one another and planar; opposed end walls 13; and a base will 14. Between opposite corners of the container, in plan view there extends a partition 15 which divides the interior of the container into a first chamber 16 and a second chamber 17. In the embodiment illustrated, the partition 15 is of curved shape e.g. an exponential curve, and approaches the rear wall 12 asymptotically so that the chamber 16 has a front to rear dimension which is a minimum at one end of the container increasing at an increasing rate as the other end of the container is approached.

At least the front wall 11, rear wall 12 and partition 15 of the container are of a transparent material, and conveniently the entire container and the partition therein may be formed as a moulding of a suitable transparent plastics material.

Behind the rear wall 12 of the container there is disposed an element 18 which is flat and which carries on its surface facing the rear wall 12 a pattern which is designed to be readily visible. As illustrated in FIG. 2, this comprises a number of dark vertical lines 19 on a light background. Extending along the length of the element 18 there is also a scale 20 of graduations.

The mode of use of the apparatus according to FIGS. 1 and 2 is that there is introduced into the chamber 16 the mixture of the first and second liquids whose relative concentration is required to be assessed. The chamber 17 is filled with the second liquid which does not contain any of the first liquid. The user of the apparatus then looks through the container from its front wall 11 to the element 18 behind the rear wall 12 thereof, in the direction of arrow 21. To the user, there will be a pan of the container, at the end thereof at which the chamber 16 is of minimum front to rear dimension at which the markings 19 on the element 18 are clearly visible as indicated at 22. At some region approaching the opposite end of the container, because the user has to look for a greater distance through the mixed liquids in the firs chamber 16, the markings 19 will not be discernable. In practice, it has been found that there is a relatively well defined region 23 at which the markings 19 become discernable due to the decreasing dimension of the chamber 16. It will be appreciated that the exact position of the region 23 along the container 10 therefore represents a measure of the concentration of the first liquid in the second liquid, which may be read off the scale 20 to provide a measure which is sufficiently accurate for many purposes such as described above.

As illustrated the element 18 is disposed behind the rear wall 12 of the container 10. It is envisaged that the container 10, which as referred to above is conveniently a plastics moulding, will be in the nature of a "throw-away" item to be discarded after the carrying out of an assessment, and the element 18 may take the form of a card which may simply be held at the rear wall 12 of the container by a user. For carrying out tests on different liquids, or on different relative concentrations of liquids, a range of different such cards may be provided, from which the user selects an appropriate one according to the nature of the liquids involved For examples such cards may differ in respect of the scale 20, or in respect of the design or pattern 19 they bear to suit different colours of liquid.

Alternatively, a visible pattern or design, and scale, could be printed on the rear wall 12 of the container.

Another way in which the apparatus may be adapted for carrying out tests on different liquids, or on different relative concentrations of liquids, is to provide an additional element between the element 18 and the rear wall 12 of the container 10, which additional element has a visual characteristic changing along its length. For example, such additional element may be clear at one end and opaque at the other end, or coloured at one end and uncoloured at the other end, thereby changing the effective aspect of the element 18. Yet another possibility is that the rear wall 12 of the container may have a visual characteristic changing along its length.

The chamber 17 which contains uncontaminated liquid acts as a lens and helps prevent my refraction errors in use of the apparatus.

Referring now to FIGS. 3 and 4 of the drawings, these show a modified embodiment of the apparatus. This embodiment comprises a container which is of the same configuration as the container 10 in FIGS. 1 and 2, behind which there is disposed a fixed element 25 which bears a scale 26 and, between the element 25 and the rear wall of the container, a member 27. The member 27 is disposed between the container and the element 25, and is supported for movement lengthwise of the container. The member 27 bears a visible pattern 28 and a pointer 29 against which the scale 26 may be read.

In use of the apparatus of FIGS. 3 and 4, the two chambers of the container 10 will be filled respectively with the contaminated liquid being assessed and with the uncontaminated clear liquid, as in the embodiment of FIG. 1. The user then looks through the container and moves the member 27 lengthwise of the container until it reaches a position at which the pattern 28 is no longer discernable. The pointer 29 then provides a reading, off the scale 26, of the relative concentration of the two liquids.

Referring now to FIG. 5 of the drawings, is shows a further embodiment of apparatus which includes a container 30 which is of the same configuration as the container 10 in FIGS. 1 to 4. At the front and rear of the container there are disposed respective arrays of radiation-emitting elements 31 and radiation receiving elements 32. By way of example, such radiation may be infra-red radiation. Depending on the relative concentration of the liquids in the mixture thereof, a greater or lesser number of the receiving elements 32 will respond to the radiation transmitted through the container, thereby providing a direct assessment of such relative concentration. Assessment using such apparatus may readily be automated using well-known electronics principles.

Figure 6:
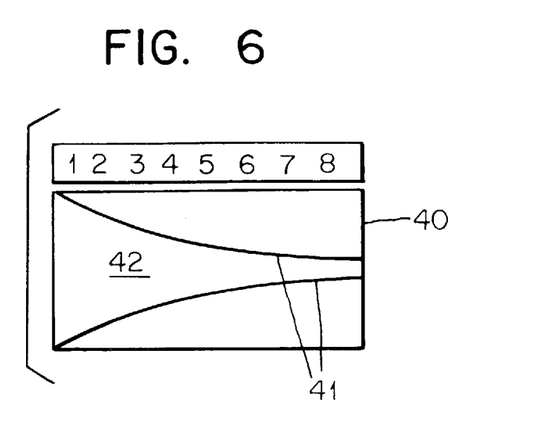
FIGS. 6 and 7 are diagrammatic plan views of yet further embodiments of apparatus according to the invention.

Referring now to FIG. 6 of the drawings, this shows in plan view a container 40 which has two internal partitions 41 to define a chamber 42 therein for receiving a liquid under investigation. The chamber 42 is thus positioned symmetrically between the front and rear walls of the container 40.

Figure 7:
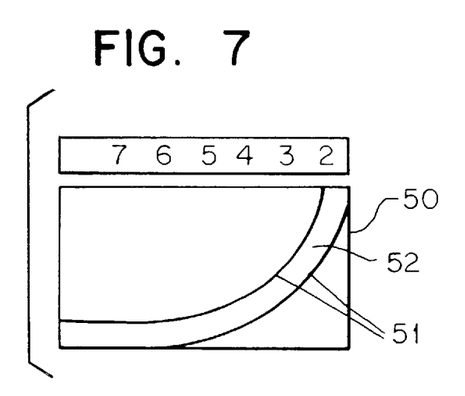

FIG. 7 shows a container 50 which is divided by two internal partitions 51 to form a chamber 52 for fluid under investigation. The shape of the partitions 51 is such that the cross sectional area of the chamber 52 varies only slightly from one end of the container to the other, thereby providing a substantially constant resistance to flow of fluid through the chamber 52 throughout the length of the chamber. When the container is viewed from front to rear, however, the dimension of the chamber 52 is substantially greater at one end of the container than at the other end Therefore the apparatus may be used in the same manner as described above, but with potential advantages in the case where a moving stream of fluid is being examined.

Figure 8:
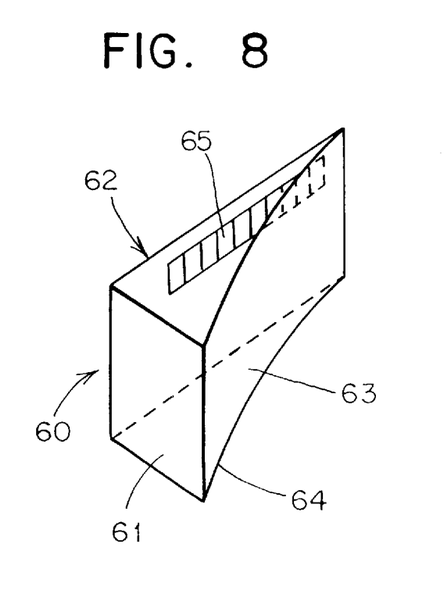
FIG. 8 is a diagrammatic perspective view of another embodiment of apparatus according to the invention.

Referring now to FIG. 8 of the drawings, there is shown an embodiment of the invention which is of somewhat simplified construction compared with the embodiments above described. It comprises a container 60 which is of somewhat wedge-shaped configuration in plan view, comprising a side wall 61, a rear wall 62 and a front wall 63 which may be curved in similar configuration to the partition 15 in the embodiment of FIGS. 1 and 2. The container has a closed base 64 and an open top for enabling a liquid for assessment to be introduced into the chamber defined by the container. A scale 65 is printed on or adhered to the rear wall 62. A means for assisting the visual assessment, e.g. a suitable pattern or the like, may be provided in addition to the scale 62.

Apparatus according to FIG. 8 is used in substantially the same manner as described above in relation to the other Figures of the drawings.

For use of apparatus according to the invention in the course of a surgical operation as above referred to, it is envisaged that the apparatus may be incorporated in or provided in operative association with a disposable catheter or catheter bag. For example, the apparatus may be provided internally of a transparent catheter bag, arranged so that liquid contained in the bag can enter the chamber of the apparatus and the user can look through the apparatus to assess the liquid contained therein. Alternatively, the apparatus could be provided externally of a catheter bag, there being provided means affording a connection for flow of liquid from the catheter bag into the chamber of the apparatus. A further possibility is that all or part of a quantity of liquid flowing through a catheter may be arranged to flow through the chamber of the apparatus.

Figure 9:
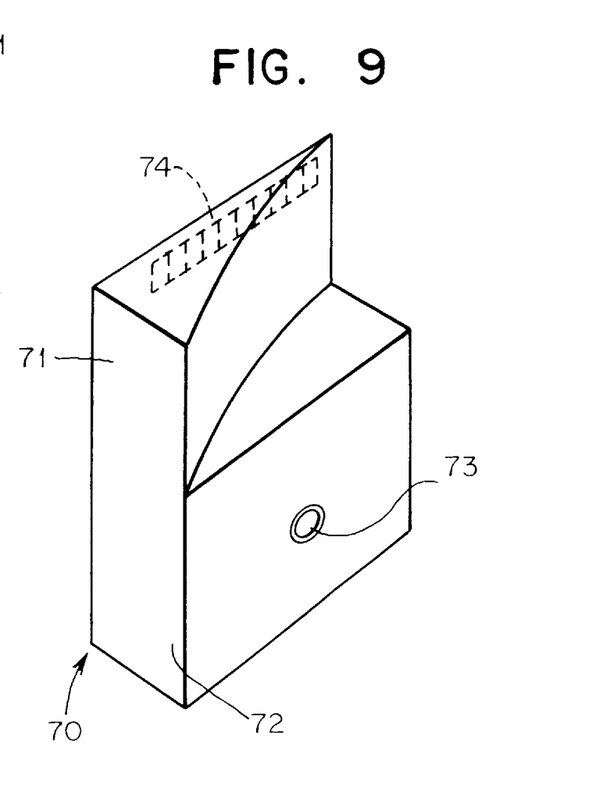
FIG. 9 is a diagrammatic perspective view of yet a further embodiment of apparatus according to the invention.

Referring now to FIG. 9 of the drawings, this shows an embodiment of the invention which is adapted to carry out a particular assessment, namely that of estimating the hemoglobin concentration in the blood of a patient. The apparatus comprises a closed container 70 of which a portion, 71, is in the configuration of the device shown in FIG. 8 but with a closed top and open bottom, and a portion 72 is generally of rectangular configuration in elevation and plan communicating with the container portion 71. Together, the two portions of the container define a chamber whose total volume may be approximately 50 ml. One wail of the container, e.g. as illustrated part of the portion 72, is provided with an injection port 73 which may be in the form of a diaphragm, e.g. of rubber, enabling introduction of a liquid into the interior of the container by use of a hypodermic syringe.

Apparatus as shown in FIG. 9 would be supplied filled with a dilutant liquid, e.g. a saline solution. A measured quantity of patients blood would be injected into the apparatus through the port 73, e.g. 0.2 ml of blood. To mix the blood thoroughly with the saline solution, the apparatus would be agitated and it may contain a movable agitator member, e.g. a plastics ball or the like to assist mixing. The part 71 would then be looked through and the scale 74 observed in the manner above described, to provide an indication of hemoglobin concentration. When apparatus is supplied specifically for such a test, the scale 74 could be calibrated directly in hemoglobin concentration, eg in grams/100 ml.

Figure 10:
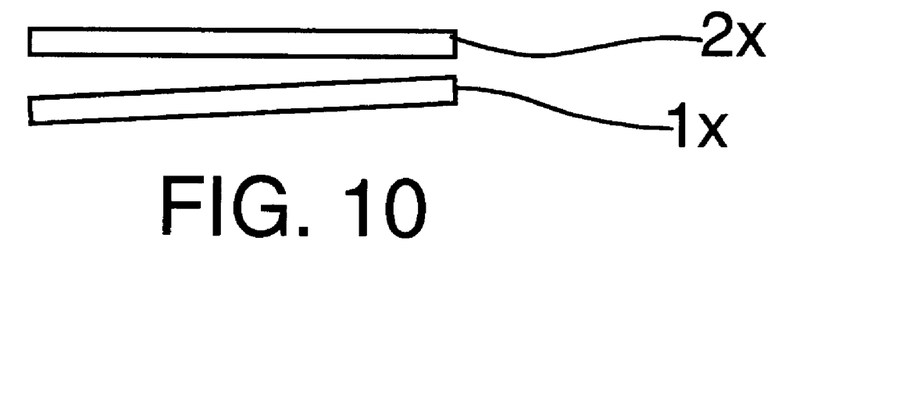
FIG. 10 is a diagrammatic plan view of a further embodiment of the apparatus according to the invention.

Referring now to FIG. 10 an alternative embodiment of the apparatus of the invention is shown it comprises, essentially, a chamber 1x which is essentially elongate and has equally spaced front and rear walls. Positioned rearward of chamber 1x is a pattern or marker 2x for examining the effect of transmission of radiation through fluid in chamber 1x. Notably, chamber 1x and pattern 2x are of approximately equal lengths but are positioned, with respect to one another, at varying distances. Thus towards the right hand side of FIG. 10 chamber 1x and pattern 2x are at their closest spacing whereas towards the left hand side of FIG. 10 chamber 1x and pattern 2x are furthest apart. The gap between chamber 1x and pattern 2x may be air filled or, alternatively, filled with material that allows the selected radiation to pass therethrough for example where the radiation to be used is visible radiation the material is a transparent material or a translucent material.

In use, because of the relatively thin nature of chamber 1x fluid is drawn therein by capillary action. Thereafter, radiation of a selected type, such as visible radiation is projected onto the apparatus and as the turbidity of fluid in chamber 1x increases, typically due to increasing concentration of a component therein, the pattern, as one views from right to left, becomes increasing obliterated. Thus the point at which the pattern is obliterated can be used as marker of concentration of said component in said fluid.

Figure 11:
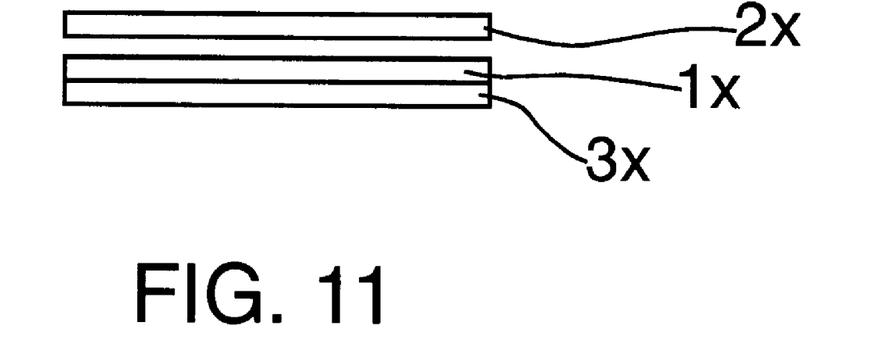
FIG. 11 is a diagrammatic plan view of a further embodiment of the apparatus according to the invention.

FIG. 11 shows an alternative embodiment of the invention where, again, a chamber 1x has equally spaced front and rear walls and provided, rearwardly thereof, is a pattern or marker 2x. However, in this instance, pattern or marker 2x is of a constant nature and thus in the instance where the radiation is visible radiation the pattern may be a bar of constant brightness or colour. Positioned forwardly of chamber 1x is a window 3x. Window 3x varies in transmissibility from one end to another. Thus towards the right hand side of FIG. 11 window 3x is relatively transmissible whereas the left hand side of FIG. 11 window 3x is much less transmissible in between there exists a graduation in transmissibility.

In the instance where the apparatus is to be used with visible light window 3x will be of variable transparency, ideally increasing or decreasing in transparency from a first end to a second end.

In use, chamber 1x is filed with a fluid containing an unknown concentration of a component and, in the instance where visible light is used, visible light is shone through window 3x and chamber 1x onto pattern 2x. As one views the apparatus from right to left one will read a point at which pattern 2x is no longer visible. This point provides an indication of the radiation-absorbing quality of the fluid which is used to determine the concentration of a component therein. Thus the apparatus provides a means for measuring the concentration of the component in the fluid.

Figure 12:
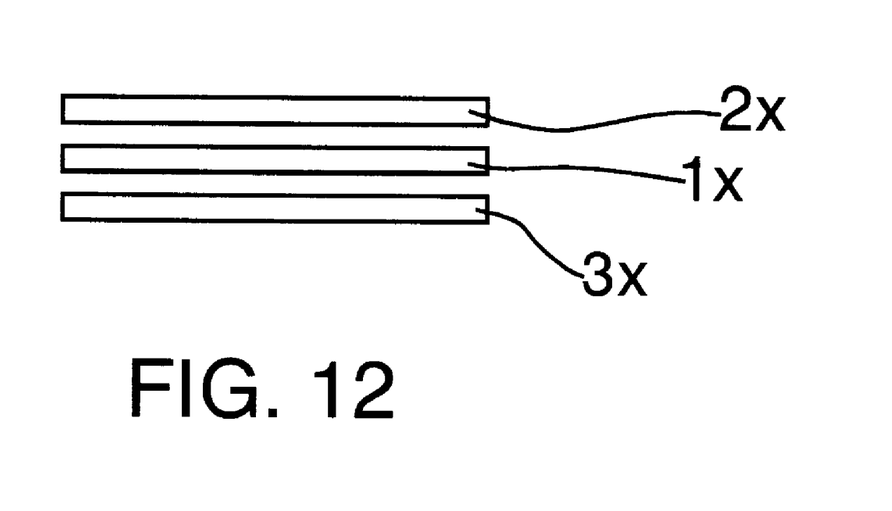
FIG. 12 is a diagrammatic plan view of a further embodiment of the apparatus according to the invention.

In FIG. 12 there is shown yet a further embodiment of the invention which comprises a chamber 1x having front and rear walls which are equally spaced, and rearward thereof a pattern or marker 2x. In addition, forward of chamber 1x there is provided a front window 3x. In this embodiment of the invention the transmissibility of window 3x is relatively constant along its length, but the degree of constant transmissibility maybe selected having regard to the requisite sensitivity of the apparatus. Pattern 2x is, however, of a variable nature in that, for example in instances where visible light is to be used the brightness or colour intensity of the pattern may vary along its length. For example pattern 2x may consist of a graduated scale such as a series of numbers from 1 to x etc of varying brightness or colour intensity. Thus towards the right hand of FIG. 12 there is shown a front view of pattern 2x which towards its right hand side is either relatively light in shade or of a light colour, and towards its left hand side is relatively dark in shade or of a dark colour.

In use, chamber 1x is filled with a fluid containing a component whose concentration is to be determined and radiation, such as visible light is shone through front window 3x and chamber 1x on to pattern 2x. The point at which pattern 2x is no longer viewable from right to left (or left to right depending upon the orientation of the pattern) provides an indication of the radiation-absorbing quality of the fluid and thus a measure of the concentration of the component in the fluid.

Figure 13:
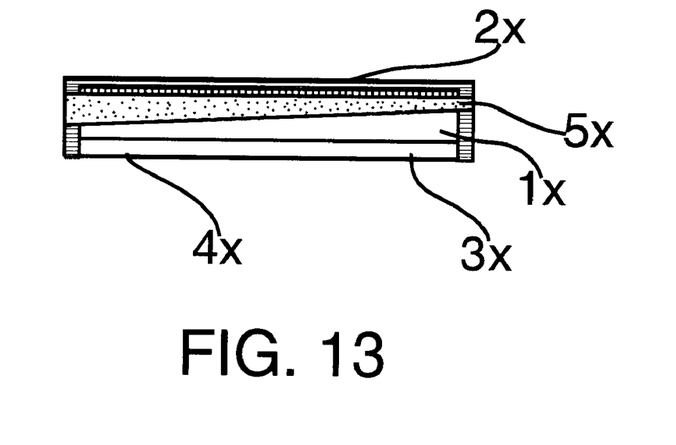
FIG. 13 is a diagrammatic plan view of a further embodiment of the apparatus according to the invention.

Referring to FIG. 13 there is shown yet a further embodiment of the invention. The embodiment comprises a chamber 1x having front and rear walls which are differently spaced with respect to each other so as provide for a variable depth chamber.

Whilst a variable depth chamber is shown in FIG. 13 it is within the scope of the invention to include a constant depth chamber in this particular embodiment of the invention.

Rearward of chamber 1x is a void 5x which may be either air filled or filled with transmissible material such as in one example a translucent plastic spacer. The purpose of the void is to determine the distance between chamber 1x and the rearmost pattern or marker 2x. Ideally, the distance is such that pattern 2x is at variable distance from chamber 1x.

Foreward of chamber 1x there is provided a front window 3x which may be of constant or variable transmissibility depending upon the requisite sensitivity of the system. Moreover, where window 3x is of constant transmissibility the degree of constant transmissibility, such as constant transparency is selected having regard to the requisite sensitivity of the system.

Foremost of window 3x is a scattering device 4x which is designed for controlling the scattering of radiation. Thus the surface irregularity of this device varies with the length of the apparatus.

In use, chamber 1x is filled with a fluid comprising a component whose concentration is to be determined and a selected form of radiation such as visible radiation, is shone through members 4x, 3x, 1x, 5x and 2x, sequentially, so that a user can determine a point at which pattern 2x is no longer visible along the length of chamber 1x. At this point one is provided with an indication of the radiation-absorbing quality of the fluid within chamber 1x and thus an indication of the concentration of the component in the fluid.

Figure 14:
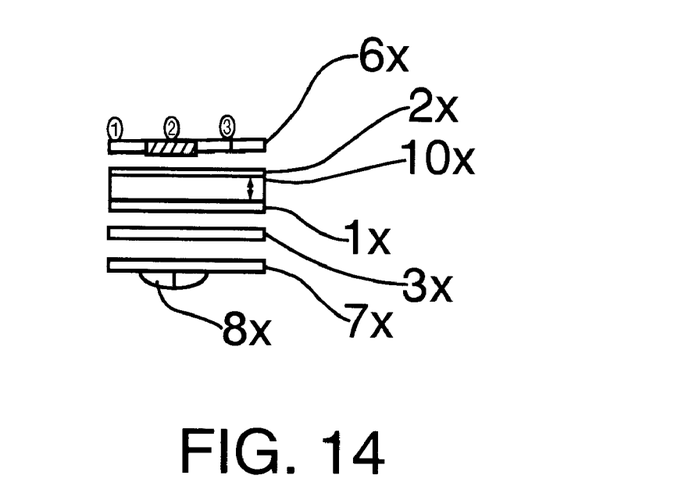
FIG. 14 is a diagrammatic cross-section view of a further embodiment of the apparatus according to the invention showing selected features of the apparatus.

Referring now to FIG. 14 there is shown yet a further embodiment of the invention. This embodiment comprises a chamber 1x which, as above described, may be of a constant or variable depth.

Positioned rearward of chamber 1x is a pattern or marker 2x whose positioning with regard to the rear wall of chamber 1x may be either constant or variable along the longitudinal axis of chamber 1x as indicated by arrows 10x. Moreover, the nature of pattern 2x may be constant or variable, that is to say where the pattern is a colour the nature of the colour may vary along the length of pattern 2x. Alternatively the pattern may consist of a graduated scale such as a series of numbers from 1 to x etc. Alternatively, the brightness or density of the colour may vary along the length of pattern 2x.

Rearward of pattern or marker 2x is a rear wall 6x whose function is to modify light entry into the rear chamber. Typically, this rear wall is opaque so as to prevent light entering via the rear into the chamber. Alternatively, it may be transparent so as to allow sunlight to enter and indeed the transparency may be constant along the length of rear wall 6x or alternatively may be variable along its length. Alternative yet again the rear wall may be reflective.

Foremost of chamber 1x, is window 3x which allows pattern 2x to be detected or viewed through the fluid. In the instance where visible light is used with the apparatus the chamber window may be transparent or translucent and of a constant or variable nature along its length. Alternatively again the front window may be selectively removable so that windows of a different nature can be used with the embodiment of the invention. For example windows of a more or less transparent nature, either of constant or variable transparency along their length, may be selectively used in this embodiment of the invention.

Foremost of front window 3x is a scale 7x which is used to directly measure the concentration of a component in the substance. Ideally, the scale is adapted to be altered so as to provide for use of the invention with a wide range of concentrations. Ideally, scale 7x is provided with a cursor 8x with which a determination can be made as to whereat the pattern or marker is no longer visible. Cursor 8x is ideally provided with information indicating that the cursor should be positioned at the point at which visibility of pattern 2x is not discernable.

It will be apparent from the above description that the invention provided by way of a selection of a combination of features which in totality acts along the length of chamber 1x so as to progressively facilitate, or hinder, an examination of the passage of radiation through a fluid contained in chamber 1x.

Thus the features disclosed in the foregoing description, or the following claims, or the accompanying drawings, expressed in their specific forms or in terms of a means for performing the disclosed function, or a method or process for attaining the disclosed result, as appropriate, may, separately or in any combination of such features, be utilised for realising the invention in diverse forms thereof.

I claim:

1. An apparatus for assessing a characteristic of a fluid in respect to its effect on the transmission of radiation through the fluid, comprising a chamber for receiving the fluid, said chamber including wall portions, arranged for passage of radiation therethrough and through the fluid between said wall portions, and fixed means for examining the effect of transmission of the radiation through the fluid at different parts of the chamber, said fixed means being fixed in use to said chamber, and said fixed means being adapted along at least one preselected axis so as to progressively facilitate an examination of the passage of radiation through the fluid whereby said characteristic can be assessed.

2. Apparatus according to claim 1 wherein said fixed means comprises a pattern or marker which is spaced differently from said chamber along a preselected axis of said pattern or marker.

3. Apparatus according to claim 1 wherein said fixed means comprises a pattern or marker of a variable nature along at least one preselected axis.

4. Apparatus according to claim 3 wherein said variable nature is progressive.

5. Apparatus according to claim 4 wherein said progressive variation is uniform.

6. Apparatus according to claim 3 wherein said pattern or marker comprises shading, coloring or density, and wherein the shading, coloring or density of said pattern or marker varies along said axis.

7. Apparatus according to claim 1 wherein said fixed means comprises a pattern or marker which is positioned to a first side to said chamber and a window which is positioned to a second side of said chamber wherein said window has a variable transmissibility along a pre-selected axis.

8. Apparatus according to claim 7 wherein the transmissibility of the window varies along said axis having regard to the type of radiation used with said apparatus.

9. Apparatus according to claim 8 wherein said transmissibility varies progressively.

10. Apparatus according to claim 9 wherein said progressive variation is uniform.

11. Apparatus according to claim 7 wherein the transparency of said window varies along said predetermined axis.

12. Apparatus according to claim 2 wherein said chamber includes wall portions that are spaced differently from one another at different parts of the chamber.

13. Apparatus according to claim 1 wherein said chamber comprises or forms part of a liquid-tight container for retaining a liquid during assessment thereof.

14. Apparatus according to claim 1 wherein said apparatus comprises a scale disposed along the chamber to provide a direct reading of concentration of a component in the fluid.

15. Apparatus according to claim 1 wherein said chamber is defined by a dividing wall portion in a container having substantially parallel opposite walls, said dividing wall portion providing a further chamber for containing uncontaminated fluid.

16. Apparatus according to claim 1 wherein said chamber comprises or forms part of a liquid-tight container for retaining a liquid during assessment thereof wherein said container includes a portion defining said chamber and a further portion in communication with said chamber, said portions together defining a predetermined volume.

17. A method of assessing a characteristic of a fluid in respect to its effect on the transmission of radiation through the fluid, said method comprising the steps of:

providing an apparatus comprising a chamber for receiving the fluid, said chamber include wall portions arranged for passage of radiation therethrough and through the fluid between said wall portions, and fixed means for examining the effect of transmission of the radiation through the fluid at different parts of the chamber, said fixed mean being fixed in use to said chamber, and said fixed means being adapted along at least one preselected axis so as to progressively facilitate an examination of the passage of radiation through the fluid whereby said characteristic can be assessed;

passing radiation through the fluid in said apparatus; and examining the effect of transmission of the radiation through the fluid at different parts of the chamber.

18. A method according to claim 17 wherein the radiation is visible or ultraviolet light and the apparatus comprises a viewable element, and the step of examining comprises observing a position in the chamber at which said viewable element is no longer clearly discernable, said position providing an assessment of the relevant characteristics of the fluid.

19. Apparatus according to claim 1 further comprising means for releasably mounting said fixed means for replacement thereof.

20. An apparatus for assessing a characteristic of a fluid in respect to its effect on the transmission of radiation through the fluid, comprising a chamber for receiving the fluid, said chamber including a front wall portion and a rear wall portion equally spaced from each other and arranged for passage of radiation therethrough and through the fluid between said front and rear wall portions, and means for examining the effect of transmission of the radiation through the fluid at different parts of the chamber, said examining means comprising a pattern or marker disposed adjacent to one of said wall portions and having a variable nature along at least one preselected axis so as to progressively facilitate an examination of the passage of radiation through the fluid whereby said characteristic can be assessed.

21. An apparatus for assessing a characteristic of a fluid in respect to its effect on the transmission of radiation through the fluid, comprising a chamber for receiving the fluid, said chamber including a front wall portion and a rear wall portion equally spaced from each other and arranged for passage of radiation therethrough and through the fluid between said front and rear wall portions, and means for examining the effect of transmission of the radiation through the fluid at different parts of the chamber, said examining means comprising a pattern or marker disposed adjacent to said rear wall portion, and a window disposed adjacent said front wall portion and having a variable transmissibility.

* * * * *